(12) United States Patent
Dales

(10) Patent No.: US 6,846,927 B1
(45) Date of Patent: Jan. 25, 2005

(54) PREPARATION OF PURINES

(75) Inventor: John Robert Mansfield Dales, Worthing (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 406 days.

(21) Appl. No.: 09/265,926

(22) Filed: Mar. 11, 1999

Related U.S. Application Data

(63) Continuation of application No. 08/732,479, filed on Oct. 18, 1996, now abandoned, which is a continuation of application No. PCT/EP95/01840, filed on Apr. 19, 1995.

(30) Foreign Application Priority Data

Apr. 19, 1994 (GB) .............................................. 9407698

(51) Int. Cl.⁷ .................... C07D 473/18; C07D 473/32; C07D 473/40
(52) U.S. Cl. ...................................... 544/276; 544/277
(58) Field of Search ................................ 544/276, 277

(56) References Cited

FOREIGN PATENT DOCUMENTS

| EP | 0141927 | 5/1985 |
|---|---|---|
| EP | 0182024 | 5/1986 |
| EP | 0302644 | 2/1989 |
| EP | 0352953 | 1/1990 |
| EP | 0369583 | 5/1990 |

OTHER PUBLICATIONS

Hackh's Chemical Dictionary, Third edition, p. 18 (1944).

*Primary Examiner*—Mark L. Berch
(74) *Attorney, Agent, or Firm*—Thomas R. Savitsky

(57) ABSTRACT

A process for the preparation of a compound of formula (A) wherein: X is hydrogen, hydroxy, chloro, $C_{1-6}$ alkoxy or phenyl $C_{1-6}$ alkoxy; and $R_a$ and $R_b$ are hydrogen, or acyl or phosphate derivatives thereof, which process comprises: (i) the preparation of a compound of formula (I) whereiff $R_1$ is $C_{1-6}$ alkyl, or phenyl $C_{1-6}$ alkyl in which the phenyl group is optionally substituted; $R_2$ is hydrogen hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group or a protected amino group, which preparation comprises the reaction of a compound of formula (II), wherein $R_2$ and $R_3$ are as defined for formula (I) with a compound of formula (V) wherein L is a leaving group and $R_1$ is as defined for formula (I), to give a compound of formula (VI), and thereafter converting the intermediate compound of formula (VI) to a compound of formula (I) via decarboxylation, and, as necessary or desired, interconverting variables $R_1$, $R_2$ and $R_3$ to further values of $R_1$, $R_2$ and $R_3$; (ii) the conversion of the resulting compound of formula (I) to a compound of formula (A) by converting variable $R_3$, when other than amino, to amino, reducing the ester groups $CO_2R_1$ to $CH_2OH$ and optionally forming acyl or phosphate derivatives thereof, and as necessary or desired converting variable $R_2$ in the compound of formula (I) to variable X in the compound of formula (A); characterized in that $R_2$ is chloro in formula (I).

2 Claims, No Drawings

PREPARATION OF PURINES

RELATED APPLICATIONS

This application is a continuation of U.S. Ser. No. 08/732,479 filed 18 Oct. 1996 now abandoned which is a continuation of the §371 national stage entry of PCT/EP95/01840, filed Apr. 19, 1995.

This invention relates to a process for the preparation of pharmaceutical compounds.

The compound 2-amino-6-chloropurine (ACP) of formula:

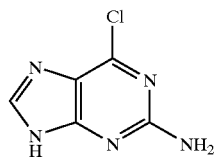

is a useful intermediate in the preparation of nucleoside analogue antiviral agents, such as penciclovir (previously known as BRL 39123) and famciclovir (previously known as BRL 42810), described in EP-A-141927 (Example 1) and EP-A-182024 (Example 2), respectively. The intermediate is 9-substituted with an appropriate side chain precursor, followed by conversion of the 6-chloro moiety to a hydroxy (a guanine) or hydrogen (a 2-aminopurine).

A process from ACP is generally described in EP-A-302644 and U.S. Pat. No. 5,175,288 and an improved process over the process specifically described in this publication has now been discovered. The key difference is that in the original process the chlorine group in the 6-position of the purine molecule is removed early in the process (see reaction Scheme 1). Significant yield and processing advantages are obtained by retaining the 6-chloro substituent in the molecule through the process, removing it only at the final step (see reaction Scheme 2). With streamlining of the process stages and removal of the column chromatography steps, which would have rendered the route disadvantageous as a production process, overall yields have been increased from 10.6% to 41%.

Accordingly, the present invention provides a process for the preparation of penciclovir/famciclovir from ACP which process comprises the process from ACP as described in EP-302644, characterised in that the 6-chloro substituent is removed subsequent to the decarboxylation and hydrolysis steps.

As no aqueous dilution is used to precipitate the product at the coupling step there is large capacity advantage, and the dimethylformamide is more easily recovered as it does not have to be separated from a large volume of water.

There are greater overall volume efficiencies in the process.

The following Examples illustrate the invention.

EXAMPLE 1

(Stage 1 Product)
Preparation of 2-amino-6-chloro-9-(methyl 2-carbomethoxybutanoate-4-yl)purine A mixture of 2-amino-6-chloropurine (9.18 g, 53.1 mmole), triethyl 3-bromopropane-1,1,1-tricarboxylate (20.33 g, 57.3 mmole), potassium carbonate (11.1 g, 80.3 mmole) and dimethylformamide (190 ml) were stirred together at 60° C. to 63° C. for 22 h. After this time the reaction mixture was filtered hot through a celite bed and the cake washed with dimethylformamide (30 ml). The filtrate and washing were combined and the solvent removed under high vacuum distillation to leave a crude reddish brown oil. This was dissolved in methanol (140 ml), cooled to 20° C. and then a solution of sodium methoxide (1.2 g) in methanol (40 ml) was added with stirring. After ca 20 minutes a precipitate formed and the stirring was continued for a total of 1 hour. The reaction mixture was then cooled to 15° C. and held at this temperature for 30 minutes. The product was filtered off and washed with methanol (10 ml) and dried at 40° C. for 16 h under vacuum.

Yield: 12.0 g of 95% purity material.

EXAMPLE 2

(Stage 2 Product)
Preparation of 9-(4-acetoxy-3-acetoxymethylbut-1-yl)-2-amino-6-chloropurine A mixture of 2-amino-6-chloro-9-(methyl 2-carbomethoxybutanoate-4-yl) purine (32.7 g, 0.1 mole), sodium borohydride (1.5 g, 0.3 mole) and methylene dichloride (125 ml) were stir at 20° C. Methanol (75 ml) was added dropwise over 2.0 hour period while the reaction temperature was maintained at 20–22° C. with cooling. The reaction mixture was left to stir for a further 1.5 h. Water (100 ml) was added followed by the dropwise addition of concentrated hydrochloric acid (20–22 ml) to pH 6.7 to 7.0 keeping the reaction temperature at 20–22° C. Methylene dichloride and methanol were removed under vacuum until a reaction volume of 150 ml was obtained. The reaction mixture was cooled to 5° C. and stirred at this temperature for 30 minutes. The resulting precipitate was filtered off and the product cake washed with cold water (20 ml). The resulting damp solid (40–50 g) was stirred with triethylamine (15 ml), 4-dimethylaminopyridine (1.0 g) in methylene dichloride (250 ml). Acetic anhydride (75 ml, 0.79 mole) was added dropwise over 20 to 30 minutes at such a rate to control the reflux. The reaction mixture was heated under reflux for a further 1.5 hours. The reaction was cooled to 20° C. and neutralised with 20% w/w sodium hydroxide solution to pH 6.4–6.5. The methylene dichloride layer was separated and the aqueous phase extracted with methylene dichloride (100 ml). The combined methylene dichloride phases were evaporated to dryness. The crude damp solid was recrystallised from 3:1 methanol:water (75 ml), cooling the precipitate to −5° C. for 1 h before filtration. The product was washed with cold 3:1 methanol:water (0° C.) and dried at 40° C. for 16 h in a vacuum oven.

Yield: 23 g of 97% to 98% purity material.

EXAMPLE 3

(Stage 3 Product)
a) Preparation or 9-(4-acetoxy-3-acetoxymethylbut-1-yl)-2-aminopurine—famciclovir A mixture of 9-(4-acetoxy-3-acetoxymethylbut-1-yl)-2-amino-6-chloropurine (15.4 g, 43 mmole), 5% palladium on carbon (6.16 g), triethylamine (6.6 ml, 47 mmole) and ethyl acetate (77 ml) was stirred at 50° C. under a hydrogen atmosphere at 1 bar pressure in an autoclave for 3 to 5 hours. After completion of the reaction the mixture was removed from the autoclave which was washed out with ethyl acetate (30 ml) keeping the washings at 50° C. The main reaction mixture was filtered through a celite bed followed by the washings and finally with ethyl acetate (30 ml). Water (46 ml) was added to the combined ethyl acetate filtrate plus washings. The ethyl acetate was evaporated to dryness to leave a crude white solid. This was recrystallised from n-butanol (62 ml), stirring the cooled solution at 0 to 5° C. for 3 h before filtration. The product was filtered off and washed with the mother liquors. The solid was reslurried in n-heptane (50 ml) stirred for 30 minutes and filtered. The product was dried at 40° C. for 16 h under vacuum.

Yield: 11–11.3 g.

b) Preparation of 9-(4-hydroxy-3-hydroxymethylbut-1-yl) guanine—penciclovir

A mixture of 9-(4-acetoxy-3-acetoxymethylbut-1-yl)-2-amino-6-chloropurine (10 g, 28.1 mmole), formic acid (96%. 6.3 ml) and water (55 ml) was stirred and heated to reflux for about 4 hours. After cooling the solution was basified by mixing with sodium hydroxide solution (12.5M, 27 ml) and the resulting solution was stirred for 1.5 hrs. The solution was neutralised by the addition of formic acid. The resultant slurry was heated to reflux (ca 105° C.) then cooled to 40–45° C. and stirred for about 3 hours. The crude product is then isolated and washed with water (20 ml). The isolated product was dissolved in sodium hydroxide solution (3M, 80 ml). Carbon (ca 1.5 g) was added and the slurry stirred for about 1 hr then the carbon was removed by filtration and washed with water (20 ml). The solution was neutralised by the addition of formic acid and the resultant precipitate was redissolved by heating to ca 100° C. and was then cooled. The precipitated product was stirred for about 3 hrs then isolated and washed with water (2×20 ml) before being dried.

Yield 5.3–5.5 g.

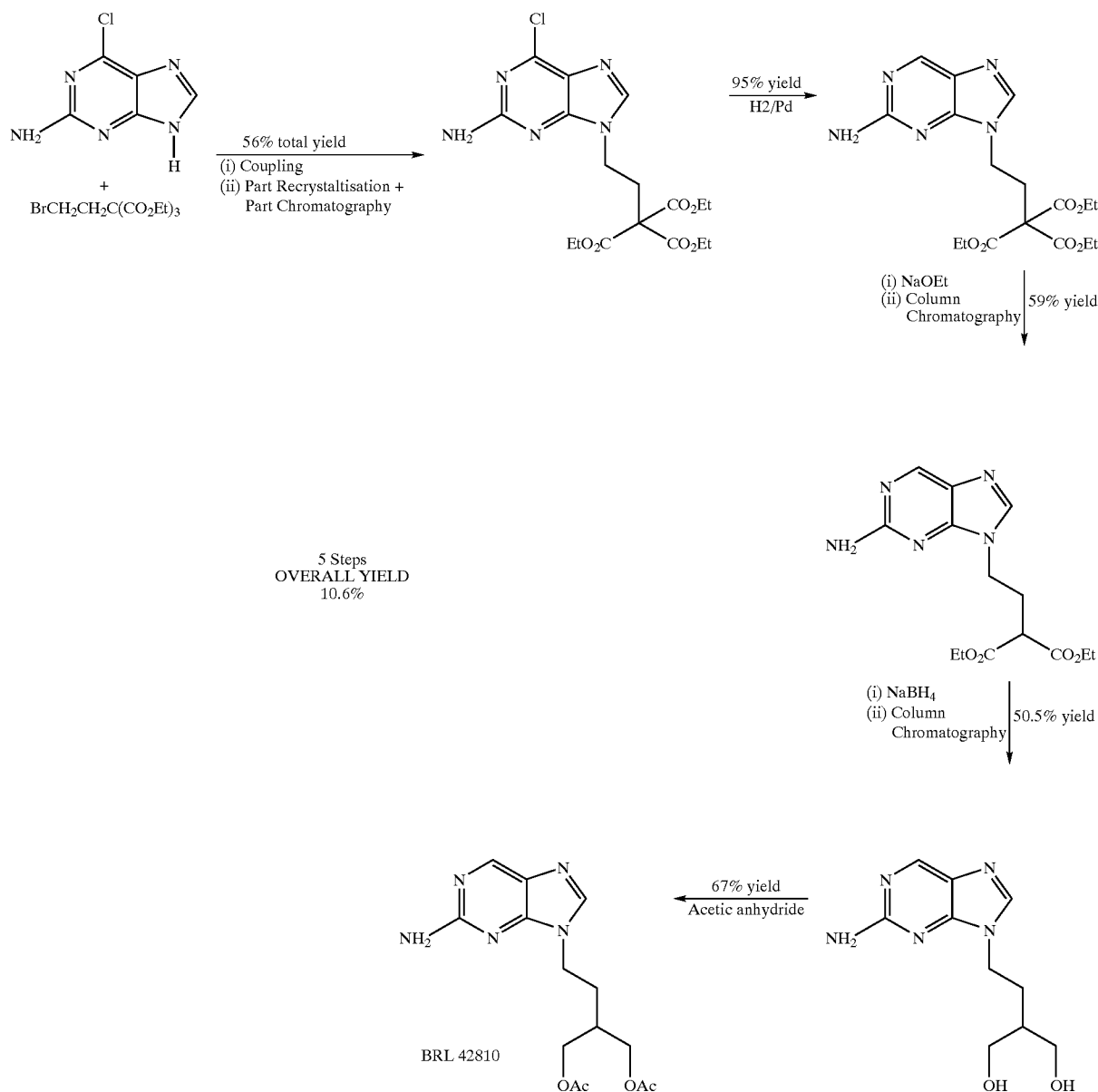

(scheme 2)

Process of the Invention

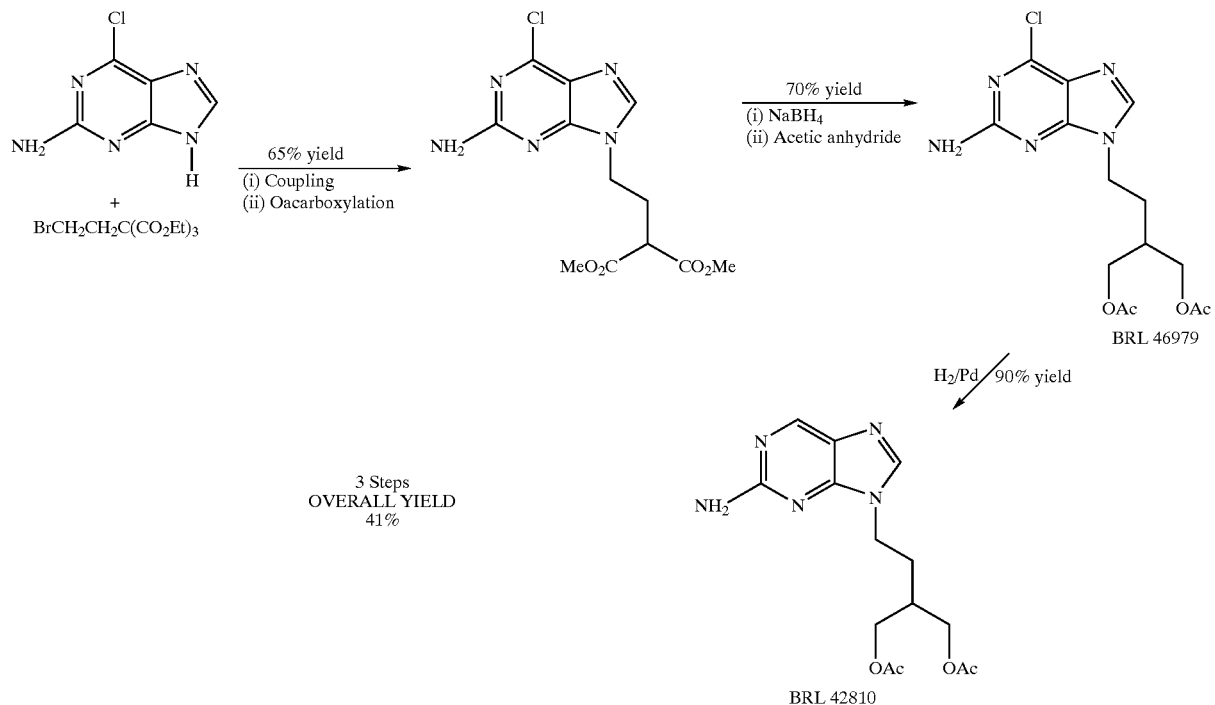

3 Steps
OVERALL YIELD
41%

What is claimed is:

1. A process for the preparation of a compound of formula (A):

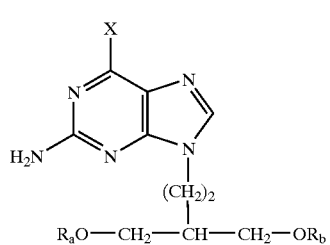

wherein
X is hydrogen or hydroxy; and $R_a$ and $R_b$ are hydrogen or acetyl, which process comprises:
(i) the preparation of a compound of formula (I):

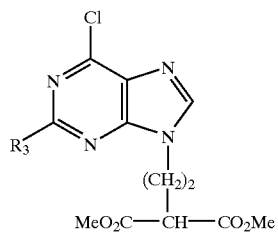

wherein $R_3$ is an amino group or a protected amino group, which preparation comprises the reaction of a compound of formula (II):

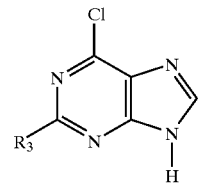

wherein $R_3$ is as defined above for formula (I) with a compound of formula (V):

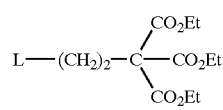

wherein L is a leaving group, to give a compound of formula (VI):

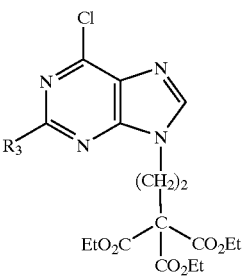

and thereafter converting the intermediate compound of formula (VI) to a compound of formula (I) via decarboxylation with sodium methoxide in methanol; and (ii) conversion of the resulting compound of formula (I) to a compound of formula (A) by:
   a) removal, if necessary, of the amino protecting group;
   b) reducing the ester groups $CO_2Me$ to $CH_2OH$ groups, and, if necessary, acetylating to form the corresponding $CH_2OAc$ groups; and
   c) dechlorinating via a hydrogenolysis reaction to yield a compound of Formula (A) in which X is hydrogen; or dechlorinating via a hydrolysis reaction to yield a compound of Formula (A) in which X is hydroxy.

2. A process for the preparation of a compound of formula (A):

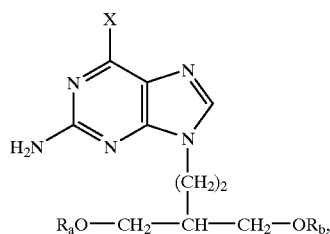

(A)

wherein

X is hydrogen or hydroxy; and $R_a$ and $R_b$ are hydrogen or acetyl, which process comprises:

(i) the preparation of a compound of formula (I):

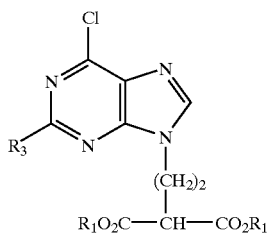

(I)

wherein $R_1$ is $C_{1-6}$alkyl or phenyl$C_{1-6}$alkyl, in which the phenyl group is optionally substituted; and $R_3$ is an amino group or a protected amino group, which preparation comprises the reaction of a compound of formula (I):

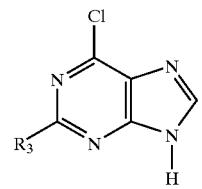

(II)

wherein $R_3$ is as defined above for formula (I), with a compound of formula (V):

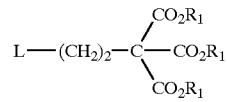

(V)

wherein

L is a leaving group; and $R_1$ is as defined above for formula (I), to give a compound of formula (VI):

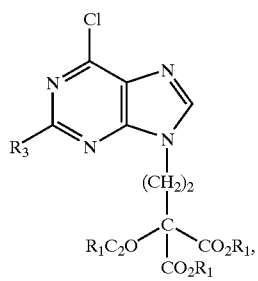

(VI)

and thereafter converting the intermediate compound of formula (VI) to a compound of formula (I) via decarboxylation; and (ii) conversion of the resulting compound of formula (I) to a compound of formula (A) by:
   a) removal, if necessary, of the amino protecting group;
   b) reducing the ester groups $CO_2R_1$ to $CH_2OH$ groups, and, if necessary, acetylating to form the corresponding $CH_2OAc$ groups; and
   c) dechlorinating via a hydrogenolysis reaction to yield a compound of formula (A), in which X is hydrogen; or dechlorinating via a hydrolysis reaction to yield a compound of formula (A), in which X is hydroxy, wherein decarboxylation of the compound of formula (VI) is effected by the addition of about 0.42 equivalents of sodium methoxide.

* * * * *